(12) United States Patent
Hushka

(10) Patent No.: US 7,384,421 B2
(45) Date of Patent: Jun. 10, 2008

(54) SLIDE-ACTIVATED CUTTING ASSEMBLY

(75) Inventor: Dylan Hushka, Boulder, CO (US)

(73) Assignee: Sherwood Services AG, Schaffhausen (CH)

( * ) Notice: Subject to any disclaimer, the term of this patent is extended or adjusted under 35 U.S.C. 154(b) by 298 days.

(21) Appl. No.: 11/239,767

(22) Filed: Sep. 30, 2005

(65) Prior Publication Data

US 2006/0074416 A1 Apr. 6, 2006

Related U.S. Application Data

(60) Provisional application No. 60/616,442, filed on Oct. 6, 2004.

(51) Int. Cl.
*A61B 18/12* (2006.01)
(52) U.S. Cl. .............................. 606/51; 606/41; 606/50
(58) Field of Classification Search ............. 606/41–52
See application file for complete search history.

(56) References Cited

U.S. PATENT DOCUMENTS

| 371,664 A | 10/1887 | Brannan et al. |
|---|---|---|
| 702,472 A | 6/1902 | Pignolet |
| 728,883 A | 5/1903 | Downes |
| 1,586,645 A | 6/1926 | Bierman |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,863,339 A * | 2/1975 | Reaney et al. ................. 30/162 |
| 3,866,610 A | 2/1975 | Kletschka |
| 3,911,766 A | 10/1975 | Fridolph et al. |

(Continued)

FOREIGN PATENT DOCUMENTS

DE 2415263 10/1975

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner*—Henry M Johnson, III

(57) ABSTRACT

An endoscopic bipolar forceps is provided. The forceps includes a housing, a shaft, a drive assembly, a handle assembly and a slide activated cutting assembly. The shaft is affixed to the housing and comprises an end effector assembly comprising two jaw members at its distal end. The drive assembly is configured to move the end effector assembly. The handle assembly is in mechanical cooperation with the drive assembly. The slide-activated cutting assembly is disposed at least partially within the housing and move a knife rod comprising a knife blade at its distal end to cut tissue along a tissue seal. A source of electrosurgical energy is adapted to connect to each jaw member to enable them to conduct energy through tissue to affect a tissue seal.

13 Claims, 8 Drawing Sheets

U.S. PATENT DOCUMENTS

| | | | |
|---|---|---|---|
| 3,920,021 A | 11/1975 | Hiltebrandt | |
| 3,921,641 A | 11/1975 | Hulka | |
| 3,938,527 A | 2/1976 | Rioux et al. | |
| 3,952,749 A | 4/1976 | Fridolph et al. | |
| 3,970,088 A | 7/1976 | Morrison | |
| 3,987,795 A | 10/1976 | Morrison | |
| 4,005,714 A | 2/1977 | Hiltebrandt | |
| 4,041,952 A | 8/1977 | Morrison, Jr. et al. | |
| 4,043,342 A | 8/1977 | Morrison, Jr. | |
| 4,074,718 A | 2/1978 | Morrison, Jr. | |
| 4,088,134 A | 5/1978 | Mazzariello | |
| 4,112,950 A | 9/1978 | Pike | |
| 4,127,222 A | 11/1978 | Adams | |
| 4,128,099 A | 12/1978 | Bauer | |
| 4,165,746 A | 8/1979 | Burgin | |
| 4,233,734 A * | 11/1980 | Bies | 30/162 |
| 4,300,564 A | 11/1981 | Furihata | |
| D263,020 S * | 2/1982 | Rau, III | D8/99 |
| 4,370,980 A | 2/1983 | Lottick | |
| 4,416,276 A | 11/1983 | Newton et al. | |
| 4,452,246 A | 6/1984 | Bader et al. | |
| 4,492,231 A | 1/1985 | Auth | |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,655,216 A | 4/1987 | Tischer | |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Xoch et al. | |
| D295,893 S | 5/1988 | Sharkany et al. | |
| D295,894 S | 5/1988 | Sharkany et al. | |
| 4,763,669 A | 8/1988 | Jaeger | |
| 4,827,929 A | 5/1989 | Hodge | |
| 4,887,612 A | 12/1989 | Esser et al. | |
| 4,938,761 A | 7/1990 | Ensslin | |
| 4,985,030 A | 1/1991 | Melzer et al. | |
| 5,007,908 A | 4/1991 | Rydell | |
| 5,026,370 A | 6/1991 | Lottick | |
| 5,084,057 A | 1/1992 | Green et al. | |
| 5,099,840 A | 3/1992 | Goble et al. | |
| 5,116,332 A | 5/1992 | Lottick | |
| 5,147,357 A | 9/1992 | Rose et al. | |
| 5,151,102 A | 9/1992 | Xamiyama et al. | |
| 5,176,695 A | 1/1993 | Dulebohn | |
| 5,190,541 A | 3/1993 | Abele et al. | |
| 5,196,009 A | 3/1993 | Kirwan, Jr. | |
| 5,197,964 A | 3/1993 | Parins | |
| 5,215,101 A | 6/1993 | Jacobs et al. | |
| 5,217,457 A | 6/1993 | Delahuerga et al. | |
| 5,217,458 A | 6/1993 | Parins | |
| 5,217,460 A | 6/1993 | Knoepfler | |
| 5,219,354 A | 6/1993 | Choudhury et al. | |
| 5,244,462 A | 9/1993 | Delahuerga et al. | |
| 5,250,047 A | 10/1993 | Rydell | |
| 5,250,063 A * | 10/1993 | Abidin et al. | 606/167 |
| 5,258,001 A * | 11/1993 | Corman | 606/167 |
| 5,258,006 A | 11/1993 | Rydell et al. | |
| 5,261,918 A | 11/1993 | Phillips et al. | |
| 5,275,615 A | 1/1994 | Rose | |
| 5,277,201 A | 1/1994 | Stern | |
| 5,282,799 A | 2/1994 | Rydell | |
| 5,290,286 A | 3/1994 | Parins | |
| 5,304,203 A | 4/1994 | El-Mallawany et al. | |
| 5,308,357 A | 5/1994 | Lichtman | |
| 5,318,589 A | 6/1994 | Lichtman | |
| 5,324,289 A | 6/1994 | Eggers | |
| 5,330,471 A | 7/1994 | Eggers | |
| 5,334,183 A | 8/1994 | Wuchinich | |
| 5,334,215 A | 8/1994 | Chen | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,344,424 A * | 9/1994 | Roberts et al. | 606/167 |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |
| 5,368,600 A | 11/1994 | Failla et al. | |
| 5,383,897 A | 1/1995 | Wholey | |
| 5,389,098 A | 2/1995 | Tsuruta et al. | |
| 5,389,104 A | 2/1995 | Hahnen et al. | |
| 5,391,166 A | 2/1995 | Eggers | |
| 5,391,183 A | 2/1995 | Janzen et al. | |
| 5,396,900 A | 3/1995 | Slater et al. | |
| 5,403,312 A | 4/1995 | Yates et al. | |
| 5,411,519 A | 5/1995 | Tovey et al. | |
| 5,411,520 A | 5/1995 | Nash et al. | |
| 5,413,571 A | 5/1995 | Katsaros et al. | |
| 5,415,657 A | 5/1995 | Taymor-Luria | |
| 5,422,567 A | 6/1995 | Matsunaga | |
| 5,423,810 A | 6/1995 | Goble et al. | |
| 5,425,739 A | 6/1995 | Jessen | |
| 5,429,616 A | 7/1995 | Schaffer | |
| 5,431,672 A * | 7/1995 | Cote et al. | 606/167 |
| 5,431,674 A | 7/1995 | Basile et al. | |
| 5,437,292 A | 8/1995 | Kipshidze et al. | |
| 5,438,302 A | 8/1995 | Goble | |
| 5,441,517 A | 8/1995 | Kensey et al. | |
| 5,443,463 A | 8/1995 | Stern et al. | |
| 5,443,464 A | 8/1995 | Russell et al. | |
| 5,443,480 A | 8/1995 | Jacobs et al. | |
| 5,445,638 A | 8/1995 | Rydell et al. | |
| 5,445,658 A | 8/1995 | Durrfeld et al. | |
| 5,451,224 A | 9/1995 | Goble et al. | |
| 5,456,684 A | 10/1995 | Schmidt et al. | |
| 5,458,598 A | 10/1995 | Feinberg et al. | |
| 5,460,629 A | 10/1995 | Shlain et al. | |
| 5,462,546 A | 10/1995 | Rydell | |
| 5,472,443 A | 12/1995 | Cordis et al. | |
| 5,478,351 A | 12/1995 | Meade et al. | |
| 5,480,409 A | 1/1996 | Riza | |
| 5,484,436 A | 1/1996 | Eggers et al. | |
| 5,496,317 A | 3/1996 | Goble et al. | |
| 5,496,347 A | 3/1996 | Hashiguchi et al. | |
| 5,499,997 A | 3/1996 | Sharpe et al. | |
| 5,509,922 A | 4/1996 | Aranyi et al. | |
| 5,514,134 A | 5/1996 | Rydell et al. | |
| 5,527,313 A | 6/1996 | Scott et al. | |
| 5,531,744 A | 7/1996 | Nardella et al. | |
| 5,536,251 A | 7/1996 | Evard et al. | |
| 5,540,684 A | 7/1996 | Hassler, Jr. | |
| 5,540,685 A | 7/1996 | Parins et al. | |
| 5,540,715 A | 7/1996 | Katsaros et al. | |
| 5,542,945 A | 8/1996 | Fritzsch | |
| 5,558,672 A | 9/1996 | Edwards et al. | |
| 5,562,699 A | 10/1996 | Heimberger et al. | |
| 5,569,241 A | 10/1996 | Edwardds | |
| 5,569,243 A | 10/1996 | Kortenbach et al. | |
| 5,571,100 A | 11/1996 | Goble et al. | |
| 5,573,424 A | 11/1996 | Poppe | |
| 5,573,534 A | 11/1996 | Stone | |
| 5,573,535 A | 11/1996 | Viklund | |
| 5,578,052 A | 11/1996 | Koros et al. | |
| 5,582,611 A | 12/1996 | Tsuruta et al. | |
| 5,585,896 A | 12/1996 | Yamazaki et al. | |
| 5,590,570 A | 1/1997 | LeMaire, III et al. | |
| 5,601,601 A | 2/1997 | Tal et al. | |
| 5,603,711 A | 2/1997 | Parins et al. | |
| 5,603,723 A | 2/1997 | Aranyi et al. | |
| 5,611,798 A | 3/1997 | Eggers | |
| 5,620,453 A * | 4/1997 | Nallakrishnan | 606/166 |

| | | | | | |
|---|---|---|---|---|---|
| 5,626,578 A | 5/1997 | Tihon | 5,954,720 A | 9/1999 | Wilson et al. |
| 5,626,609 A | 5/1997 | Zvenyatsky et al. | 5,957,923 A | 9/1999 | Hahnen et al. |
| 5,630,833 A | 5/1997 | Katsaros et al. | 5,960,544 A * | 10/1999 | Beyers ........................ 30/125 |
| 5,637,110 A | 6/1997 | Pennybacker et al. | 5,961,514 A | 10/1999 | Long et al. |
| 5,643,294 A | 7/1997 | Tovey et al. | 5,976,132 A | 11/1999 | Morris |
| 5,647,869 A | 7/1997 | Goble et al. | 5,984,939 A | 11/1999 | Yoon |
| 5,647,871 A | 7/1997 | Levine et al. | 5,989,277 A | 11/1999 | LeMaire, III et al. |
| 5,649,959 A | 7/1997 | Hannam et al. | 6,004,335 A | 12/1999 | Vaitekunas et al. |
| 5,658,281 A | 8/1997 | Heard | 6,010,516 A | 1/2000 | Hulka et al. |
| 5,662,667 A | 9/1997 | Knodel | 6,024,741 A | 2/2000 | Williamson et al. |
| 5,665,100 A | 9/1997 | Yoon | 6,024,744 A | 2/2000 | Kese et al. |
| 5,667,526 A | 9/1997 | Levin | 6,030,384 A | 2/2000 | Nezhat |
| 5,674,220 A | 10/1997 | Fox et al. | 6,033,399 A | 3/2000 | Gines |
| 5,681,282 A | 10/1997 | Eggers et al. | 6,039,733 A | 3/2000 | Buysse et al. |
| 5,693,051 A | 12/1997 | Schulze et al. | 6,041,679 A | 3/2000 | Slater et al. |
| 5,695,522 A | 12/1997 | LeMaire, III et al. | 6,050,996 A | 4/2000 | Schmaltz et al. |
| 5,700,261 A | 12/1997 | Brinkerhoff | 6,053,914 A | 4/2000 | Eggers et al. |
| 5,702,390 A | 12/1997 | Austin et al. | 6,053,933 A | 4/2000 | Balazs et al. |
| 5,707,369 A | 1/1998 | Vaitekunas et al. | D424,694 S | 5/2000 | Tetzlaff et al. |
| 5,709,680 A | 1/1998 | Yates et al. | D425,201 S | 5/2000 | Tetzlaff et al. |
| 5,716,366 A | 2/1998 | Yates | 6,059,782 A | 5/2000 | Novak et al. |
| 5,720,744 A | 2/1998 | Eggleston et al. | RE36,795 E | 7/2000 | Rydell |
| 5,727,428 A | 3/1998 | LeMaire, III et al. | 6,083,223 A | 7/2000 | Baker |
| 5,735,848 A | 4/1998 | Yates et al. | 6,086,586 A | 7/2000 | Hooven |
| 5,743,906 A | 4/1998 | Parins et al. | 6,090,107 A | 7/2000 | Borgmeier et al. |
| 5,755,717 A | 5/1998 | Yates et al. | 6,096,037 A | 8/2000 | Mulier et al. |
| 5,766,130 A | 6/1998 | Selmonosky | 6,099,550 A | 8/2000 | Yoon |
| 5,766,166 A | 6/1998 | Hooven | 6,102,909 A | 8/2000 | Chen et al. |
| 5,766,170 A | 6/1998 | Eggers | 6,110,171 A | 8/2000 | Rydell |
| 5,769,849 A | 6/1998 | Eggers | 6,113,596 A | 9/2000 | Hooven et al. |
| 5,772,655 A | 6/1998 | Bauer et al. | 6,113,598 A | 9/2000 | Baker |
| 5,772,670 A | 6/1998 | Brosa | 6,117,158 A | 9/2000 | Measamer et al. |
| 5,776,128 A | 7/1998 | Eggers | 6,123,701 A | 9/2000 | Nezhat |
| 5,776,130 A | 7/1998 | Buysse et al. | H1904 H | 10/2000 | Yates et al. |
| 5,779,701 A | 7/1998 | McBrayer et al. | 6,126,658 A | 10/2000 | Baker |
| 5,792,137 A | 8/1998 | Carr et al. | 6,152,923 A | 11/2000 | Ryan |
| 5,792,177 A | 8/1998 | Kaseda | 6,162,220 A | 12/2000 | Nezhat |
| 5,797,927 A | 8/1998 | Yoon | 6,174,309 B1 | 1/2001 | Wrublewski et al. |
| 5,797,938 A | 8/1998 | Paraschac et al. | 6,179,834 B1 | 1/2001 | Buysse et al. |
| 5,797,958 A | 8/1998 | Yoon | 6,179,837 B1 | 1/2001 | Hooven |
| 5,800,449 A | 9/1998 | Wales | 6,183,467 B1 | 2/2001 | Shapeton et al. |
| 5,807,393 A | 9/1998 | Williamsom, IV et al. | 6,187,003 B1 | 2/2001 | Buysse et al. |
| 5,810,808 A | 9/1998 | Eggers | 6,190,386 B1 | 2/2001 | Rydell |
| 5,810,811 A | 9/1998 | Yates et al. | 6,193,718 B1 | 2/2001 | Kortenbach et al. |
| 5,810,877 A | 9/1998 | Roth et al. | 6,206,876 B1 | 3/2001 | Levine et al. |
| 5,814,043 A | 9/1998 | Shapeton | 6,206,877 B1 | 3/2001 | Kese et al. |
| 5,817,093 A | 10/1998 | Williamson, IV et al. | 6,217,602 B1 | 4/2001 | Redmon |
| 5,820,630 A | 10/1998 | Lind | 6,221,039 B1 | 4/2001 | Durgin et al. |
| 5,827,271 A | 10/1998 | Buysse et al. | 6,224,593 B1 | 5/2001 | Ryan et al. |
| 5,827,279 A | 10/1998 | Hughett et al. | 6,228,080 B1 | 5/2001 | Gines |
| 5,827,281 A | 10/1998 | Levin | 6,228,083 B1 | 5/2001 | Lands et al. |
| 5,833,690 A | 11/1998 | Yates et al. | 6,267,761 B1 | 7/2001 | Ryan |
| 5,843,080 A | 12/1998 | Fleenor et al. | 6,270,497 B1 | 8/2001 | Sekino et al. |
| 5,849,022 A | 12/1998 | Sakashita et al. | 6,270,508 B1 | 8/2001 | Klieman et al. |
| 5,853,412 A | 12/1998 | Mayenberger | 6,273,887 B1 | 8/2001 | Yamauchi et al. |
| 5,860,976 A | 1/1999 | Billings et al. | 6,277,117 B1 | 8/2001 | Tetzlaff et al. |
| 5,876,401 A | 3/1999 | Schulze et al. | 6,280,458 B1 | 8/2001 | Boche et al. |
| 5,891,141 A | 4/1999 | Rydell | 6,283,961 B1 | 9/2001 | Underwood et al. |
| 5,891,142 A | 4/1999 | Eggers et al. | D449,886 S | 10/2001 | Tetzlaff et al. |
| 5,893,863 A | 4/1999 | Yoon | 6,322,561 B1 | 11/2001 | Eggers et al. |
| 5,893,875 A | 4/1999 | O'Connor et al. | 6,334,860 B1 | 1/2002 | Dorn |
| 5,893,877 A | 4/1999 | Gampp, Jr. et al. | 6,334,861 B1 | 1/2002 | Chandler et al. |
| 5,902,301 A | 5/1999 | Olig | 6,345,532 B1 | 2/2002 | Coudray et al. |
| 5,906,630 A | 5/1999 | Anderhub et al. | 6,350,264 B1 | 2/2002 | Hooven |
| 5,908,420 A | 6/1999 | Parins et al. | 6,352,536 B1 | 3/2002 | Buysse et al. |
| 5,908,432 A * | 6/1999 | Pan ........................ 606/167 | 6,358,249 B1 | 3/2002 | Chen et al. |
| 5,911,719 A | 6/1999 | Eggers | D457,958 S | 5/2002 | Dycus et al. |
| 5,913,874 A | 6/1999 | Berns et al. | D457,959 S | 5/2002 | Tetzlaff et al. |
| 5,921,984 A | 7/1999 | Sutcu et al. | 6,387,094 B1 | 5/2002 | Eitenmuller |
| 5,925,043 A | 7/1999 | Kumar et al. | 6,398,779 B1 | 6/2002 | Buysse et al. |
| 5,935,126 A | 8/1999 | Riza | 6,402,747 B1 | 6/2002 | Lindemann et al. |
| 5,944,718 A | 8/1999 | Austin et al. | 6,409,728 B1 | 6/2002 | Ehr et al. |
| 5,951,549 A | 9/1999 | Richardson et al. | H2037 H | 7/2002 | Yates et al. |

| | | |
|---|---|---|
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,511,480 B1 | 1/2003 | Tetzlaff et al. |
| 6,527,771 B1 | 3/2003 | Weadock et al. |
| 6,585,735 B1 | 7/2003 | Frazier et al. |
| 6,602,252 B2 | 8/2003 | Mollenauer |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,682,527 B2 | 1/2004 | Strul |
| 6,682,528 B2 | 1/2004 | Frazier et al. |
| 6,685,724 B1 | 2/2004 | Haluck |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,743,229 B2 | 6/2004 | Buysse et al. |
| 6,757,977 B2 * | 7/2004 | Dambal et al. ............... 30/162 |
| 6,770,072 B1 | 8/2004 | Truckai et al. |
| 6,773,434 B2 | 8/2004 | Ciarrocca |
| 6,776,780 B2 | 8/2004 | Mulier et al. |
| 6,790,217 B2 | 9/2004 | Schulze et al. |
| D496,997 S | 10/2004 | Dycus et al. |
| 6,802,843 B2 | 10/2004 | Truckai et al. |
| D499,181 S | 11/2004 | Dycus et al. |
| 6,818,000 B2 | 11/2004 | Muller et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,942,662 B2 | 9/2005 | Goble et al. |
| 6,960,210 B2 | 11/2005 | Lands et al. |
| 6,964,662 B2 | 11/2005 | Kidooka |
| 6,994,707 B2 | 2/2006 | Ellman et al. |
| 7,011,657 B2 | 3/2006 | Truckai et al. |
| 7,033,354 B2 | 4/2006 | Keppel |
| 7,052,496 B2 | 5/2006 | Yamauchi |
| D525,361 S | 7/2006 | Hushka |
| 7,083,618 B2 | 8/2006 | Couture et al. |
| 7,090,673 B2 | 8/2006 | Dycus et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,118,570 B2 | 10/2006 | Tetzlaff et al. |
| 7,118,587 B2 | 10/2006 | Dycus et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,265 B2 | 5/2007 | Keppel |
| 7,232,440 B2 | 6/2007 | Dumbauld et al. |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0040745 A1 * | 2/2003 | Frazier et al. ............... 606/51 |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0158269 A1 * | 8/2004 | Holman ............... 606/167 |
| 2004/0162557 A1 | 8/2004 | Tetzlaff et al. |
| 2004/0176762 A1 | 9/2004 | Lawes et al. |
| 2004/0193153 A1 | 9/2004 | Sarter et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2005/0004564 A1 | 1/2005 | Wham et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0101951 A1 | 5/2005 | Wham et al. |
| 2005/0101952 A1 | 5/2005 | Lands et al. |

| | | | |
|---|---|---|---|
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149151 A1 | 7/2005 | Orszulak et al. |
| 2006/0064085 A1 | 3/2006 | Schechter et al. |
| 2006/0079891 A1 | 4/2006 | Arts et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaf et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |

FOREIGN PATENT DOCUMENTS

| | | |
|---|---|---|
| DE | 2627679 | 1/1977 |
| DE | 8712328 | 3/1988 |
| DE | 4303882 | 8/1994 |
| DE | 29616210 | 1/1997 |
| DE | 19751106 | 5/1998 |
| EP | 0364216 A1 | 4/1990 |
| EP | 518230 A1 | 12/1992 |
| EP | 0 541 930 B1 | 5/1993 |
| EP | 0572131 | 12/1993 |
| EP | 584787 A1 | 3/1994 |
| EP | 0589453 A2 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1301135 A | 4/2003 |
| EP | 1330991 A1 | 7/2003 |
| EP | 1486177 A2 | 6/2004 |
| EP | 1472984 A1 | 11/2004 |
| EP | 1530952 A1 | 5/2005 |
| EP | 1532932 A1 | 5/2005 |
| EP | 1632192 A1 | 3/2006 |
| EP | 1645238 A1 | 4/2006 |
| EP | 1707143 A1 | 10/2006 |
| GB | 2213416 A * | 8/1989 |
| WO | WO89/00757 | 1/1989 |
| WO | WO94/20025 | 9/1994 |
| WO | WO95/07662 | 3/1995 |
| WO | WO95/15124 | 6/1995 |
| WO | WO96/05776 | 2/1996 |
| WO | WO 96/22056 | 7/1996 |
| WO | WO97/10764 | 3/1997 |
| WO | WO 99/40861 | 8/1999 |
| WO | WO 99/66850 | 12/1999 |
| WO | WO00/24331 | 5/2000 |
| WO | WO00/47124 | 8/2000 |
| WO | WO02/07627 | 1/2002 |
| WO | WO02/080783 | 10/2002 |
| WO | WO02/080784 | 10/2002 |
| WO | WO02/080785 | 10/2002 |
| WO | WO02/080786 | 10/2002 |
| WO | WO02/080793 | 10/2002 |
| WO | WO02/080794 | 10/2002 |
| WO | WO 02/080796 | 10/2002 |
| WO | WO02/080797 | 10/2002 |
| WO | WO02/081170 | 10/2002 |
| WO | WO 03/101311 | 12/2003 |
| WO | WO2004/032777 | 4/2004 |
| WO | WO2004/073490 | 9/2004 |
| WO | WO2004/073753 | 9/2004 |
| WO | WO 2004/082495 | 9/2004 |
| WO | WO2005/004735 | 1/2005 |
| WO | WO 2005/110264 | 11/2005 |

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.

Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectommy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress 1999.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.

"Reducing Needlestick Injuries in the Operating Room" Sales/Product Literature 2001.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, □Apr. 2001 pp. 236-237.

W. Scott Helton, "LigaSure Vessel Sealing System: Revolutionary Hemostasis Product for General Surgery" Sales/Product Literature 1999.

Michael Choti, "Abdominoperineal Resection with the LigaSure Vessel Sealing System and LigaSure Atlas 20 cm Open Instrument" Innovations That Work, □Jun. 2003.

Craig Johnson, "Use of the LigaSure Vessel Sealing System in Bloodless Hemorrhoidectomy" Innovations That Work, □Mar. 2000.

Muller et al., "Extended Left Hemicotectomy Using the LigaSure Vessel Sealing System" Innovations That Work,□Sep. 1999.

Herman et al., "Laparoscopic Intestinal Resection With the LigaSure Vessel Sealing System: A Case Report" Innovations That Work,□Feb. 2002.

Carus et al., "Initial Experience With the LigaSure Vessel Sealing System in Abdominal Surgery" Innovations That Work,□Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing For Hemostasis During Gynecologic Surgery" Sales/Product Literature 1999.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olsson et al. "Radical Cystectomy in Females" Current Surgical Techniques in Urology, vol. 14, Issue 3, 2001.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

E. David Crawford "Evaluation of a New Vessel Sealing Device in Urologic Cancer Surgery" Sales/Product Literature 2000.

Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.

Dulemba et al. "Use of a Bipolar Electrothermal Vessel Sealer in Laparoscopically Assisted Vaginal Hysterectomy" Sales/Product Literature; Jan. 2004.

Johnson et al. "Evaluation of a Bipolar electrothermal Vessel Sealing Device in Hemorrhoidectomy" Sales/Product Literature; Jan. 2004.

* cited by examiner

100 # SLIDE-ACTIVATED CUTTING ASSEMBLY

CROSS-REFERENCE TO RELATED APPLICATIONS

This application claims priority to U.S. Provisional Patent Application Ser. No. 60/616,442, filed on Oct. 6, 2004, the contents of which are hereby incorporated by reference in their entirety.

BACKGROUND

The present disclosure relates to an electrosurgical forceps and more particularly, the present disclosure relates to an endoscopic bipolar electrosurgical forceps for sealing and/or cutting tissue.

TECHNICAL FIELD

Electrosurgical forceps utilize both mechanical clamping action and electrosurgical energy to affect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are inserted into the patient through a cannula, or port, which has been made with a trocar. Typical sizes for cannulas range from three millimeters to 12 millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different than electrosurgical vessel sealing. For the purposes herein, "coagulation" is defined as a process of desiccating tissue wherein the tissue cells are ruptured and/or dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

In order to effectively seal larger vessels (or tissue) two predominant mechanical parameters should be accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between about 0.001 inches and about 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as vessels become smaller.

Many known instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied the tissue may pre-maturely move prior to activation and sealing and/or a thicker, less reliable seal may be created.

It has been found that the pressure range for assuring a consistent and effective seal is between about 3 kg/cm$^2$ to about 16 kg/cm$^2$ and, preferably, within a working range of about 7 kg/cm$^2$ to about 13 kg/cm$^2$. Manufacturing an instrument which is capable of providing a closure pressure within this working range has been shown to be effective for sealing arteries, tissues and other vascular bundles.

Various force-actuating assemblies have been developed in the past for providing the appropriate closure forces to affect vessel sealing. For example, one such actuating assembly has been developed by Valleylab Inc., a division of Tyco Healthcare LP, for use with Valleylab's vessel sealing and dividing instrument commonly sold under the trademark LIGASURE ATLAS®. This assembly includes a four-bar mechanical linkage, a spring and a drive assembly which cooperate to consistently provide and maintain tissue pressures within the above working ranges. The LIGASURE ATLAS® is presently designed to fit through a 10 mm cannula and includes a bi-lateral jaw closure mechanism which is activated by a foot switch. A trigger assembly extends a knife distally to separate the tissue along the tissue seal. A rotating mechanism is associated with a distal end of the handle to allow a surgeon to selectively rotate the jaw members to facilitate grasping tissue. Co-pending U.S. application Ser. Nos. 10/179,863 and 10/116,944 and PCT Application Ser. Nos. PCT/US01/01890 and PCT/US01/11340 describe in detail the operating features of the LIGASURE ATLAS® and various methods relating thereto. The contents of all of these applications are hereby incorporated by reference herein.

Certain surgical procedures necessitate the use of pistol-like forceps, while other procedures necessitate an in-line forceps to facilitate manipulation of vessels. For the in-line version, it would be difficult to use a conventional trigger or rotary knife actuation assembly to cut tissue.

It would be desirous to develop an endoscopic vessel sealing instrument which can be utilized for a variety of surgical procedures which may require both vessel sealing and subsequent division of tissue along the tissue seal. The instrument may include a simpler and more mechanically advantageous drive assembly to facilitate grasping and manipulating vessels and tissue. In addition and particularly with respect to in-line vessel sealing instruments, it may be desirous to manufacture an instrument which includes a sliding activation trigger to advance the cutting mechanism.

SUMMARY

According to an aspect of the present disclosure, an endoscopic bipolar forceps is provided. The forceps comprise a housing, a shaft, a drive assembly, a handle assembly and a slide-activated cutting assembly. The shaft defines a longitudinal axis, is affixed to the housing and comprises an end effector assembly at its distal end. The end effector assembly comprises two jaw members. The drive assembly is configured to move at least a portion of the end effector assembly. The handle assembly comprises a movable handle which forces a drive flange into mechanical cooperation with the drive assembly to move at least a portion of the end effector assembly. The slide-activated cutting assembly is disposed at least partially within the housing. The slide-activated cutting assembly moves a knife rod, which comprises a knife blade at its distal end, to cut tissue along a tissue seal. A source of electrosurgical energy is adapted to connect to each jaw member such that the jaw members are capable of conducting energy through tissue which is held therebetween. The electrosurgical energy is administered to seal the tissue.

In an exemplary embodiment, the slide-activated cutting assembly comprises a slide trigger configured to be pushed distally to move the knife rod distally. Further, the slide trigger may be pulled proximally to move the knife rod proximally.

It is envisioned for the slide trigger to include a generally arcuate-shaped finger rest.

It is contemplated for the slide-activated cutting assembly to comprise a knife slide which facilitates translation of the knife rod. A proximal portion of the knife slide is in mechanical engagement with the slide trigger. A distal portion of the knife slide is in mechanical engagement with the knife rod.

In an embodiment of the disclosure, the slide-activated cutting assembly further comprises a collar clamp operatively connected to the knife slide. The collar clamp helps maintain alignment of the knife slide during translation of the knife rod.

In an exemplary embodiment, the slide-activated cutting assembly includes a spring in mechanical engagement with the knife slide. The spring biases the knife slide in a proximal-most position.

It is envisioned that an amount of translation of the slide trigger substantially correlates to a resulting amount of translation of the knife rod. It is also envisioned that the amount of translation of the slide trigger indirectly correlates to a resulting amount of translation of the knife rod.

It is contemplated for the forceps to include a rotating assembly. In an exemplary embodiment, the rotating assembly rotates the jaw members about the longitudinal axis defined by the shaft.

In an embodiment of the disclosure, the forceps includes a switch disposed within the housing and in electromechanical cooperation with the source of electrosurgical energy. The switch allows a user to selectively supply bipolar energy to the jaw members to affect a tissue seal.

In an exemplary embodiment, the drive assembly comprises a reciprocating sleeve. Upon activation of the movable handle, the reciprocating sleeve translates to move a jaw member relative to the other jaw member. It is envisioned for the drive assembly to include at least one spring which biases the knife rod proximally.

A slide-activated cutting assembly for use with a surgical instrument is also disclosed. The slide-activated cutting assembly comprises a slide trigger and a knife assembly. The slide trigger comprises a flange. The knife assembly comprises a knife slide, a cutter collar, a knife rod and a collar clamp. The knife slide comprises a proximal portion which is in mechanical cooperation with the flange of the slide trigger and also comprises distal portion. The cutter collar is operatively connected with the distal portion of the knife slide. The knife rod extends distally from the cutter collar. The collar clamp maintains alignment of the knife assembly during translation of the knife rod and is positioned adjacent the cutter collar. The slide trigger and the knife assembly mutually cooperate to translate the knife rod upon translation of the slide trigger.

BRIEF DESCRIPTION OF THE DRAWINGS

Various embodiments of the subject instrument are described herein with reference to the drawings wherein.

DETAILED DESCRIPTION

Figure 1:
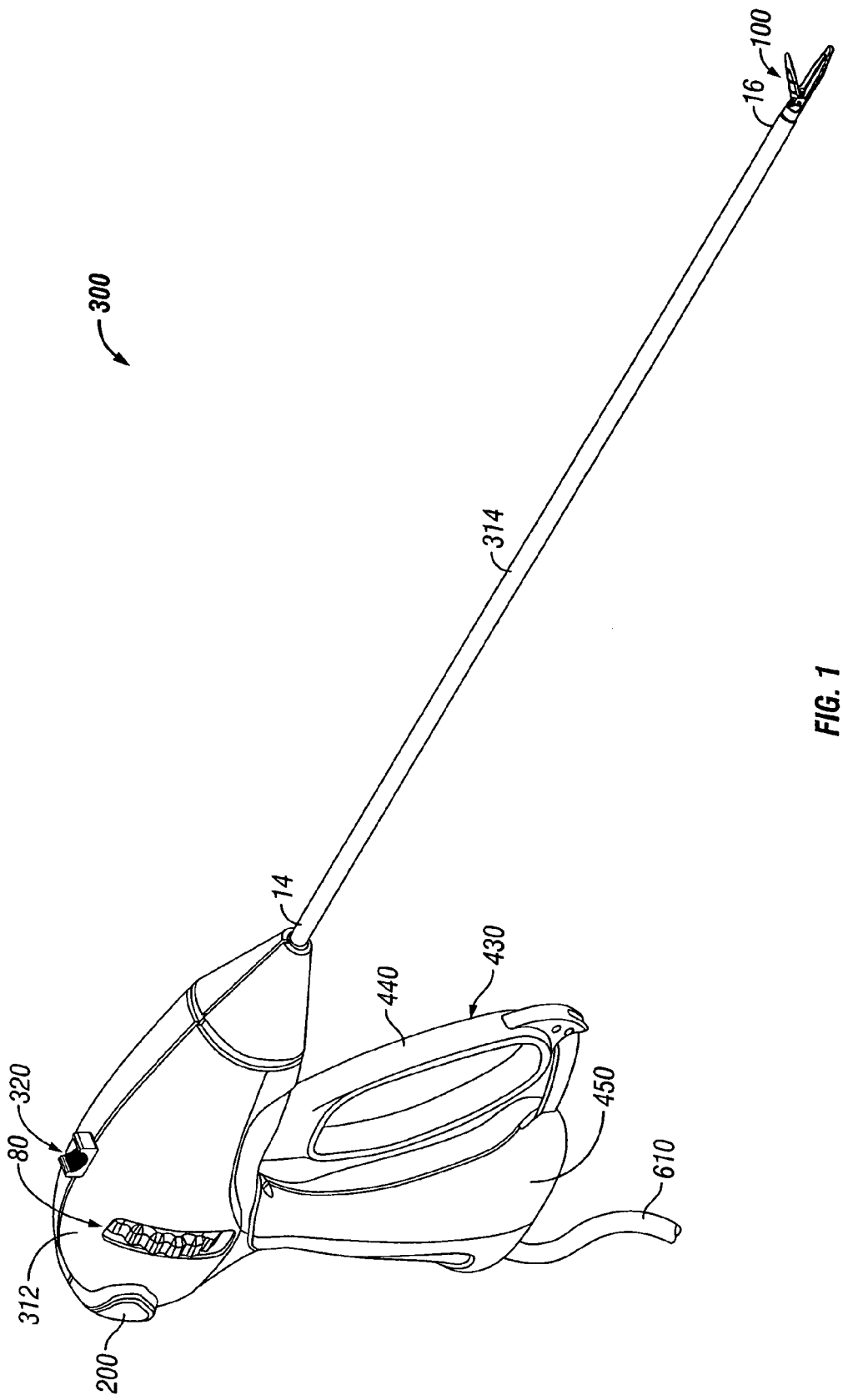
FIG. 1 is a perspective view of an endoscopic forceps according to an embodiment of the present disclosure.

Embodiments of the presently disclosed slide-activated cutting assembly will now be described in detail with reference to the drawing figures wherein like reference numerals identify similar or identical elements. As used herein and as is traditional, the term "distal" refers to that portion which is farthest from the user while the term "proximal" refers to that portion which is closest to the user.

Figure 2:
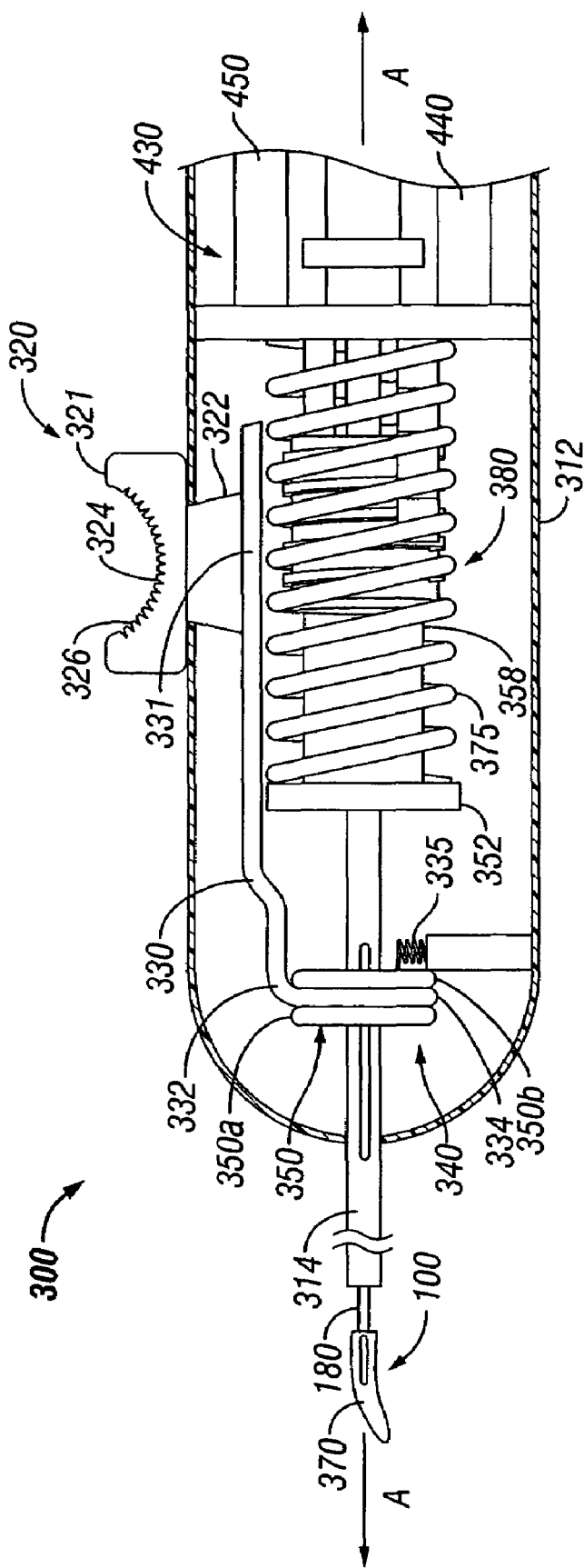
FIG. 2 is an enlarged schematic cross-sectional view of the endoscopic forceps of FIG. 1, illustrating a slide-activated cutting assembly comprising a slide trigger.
Figure 3:
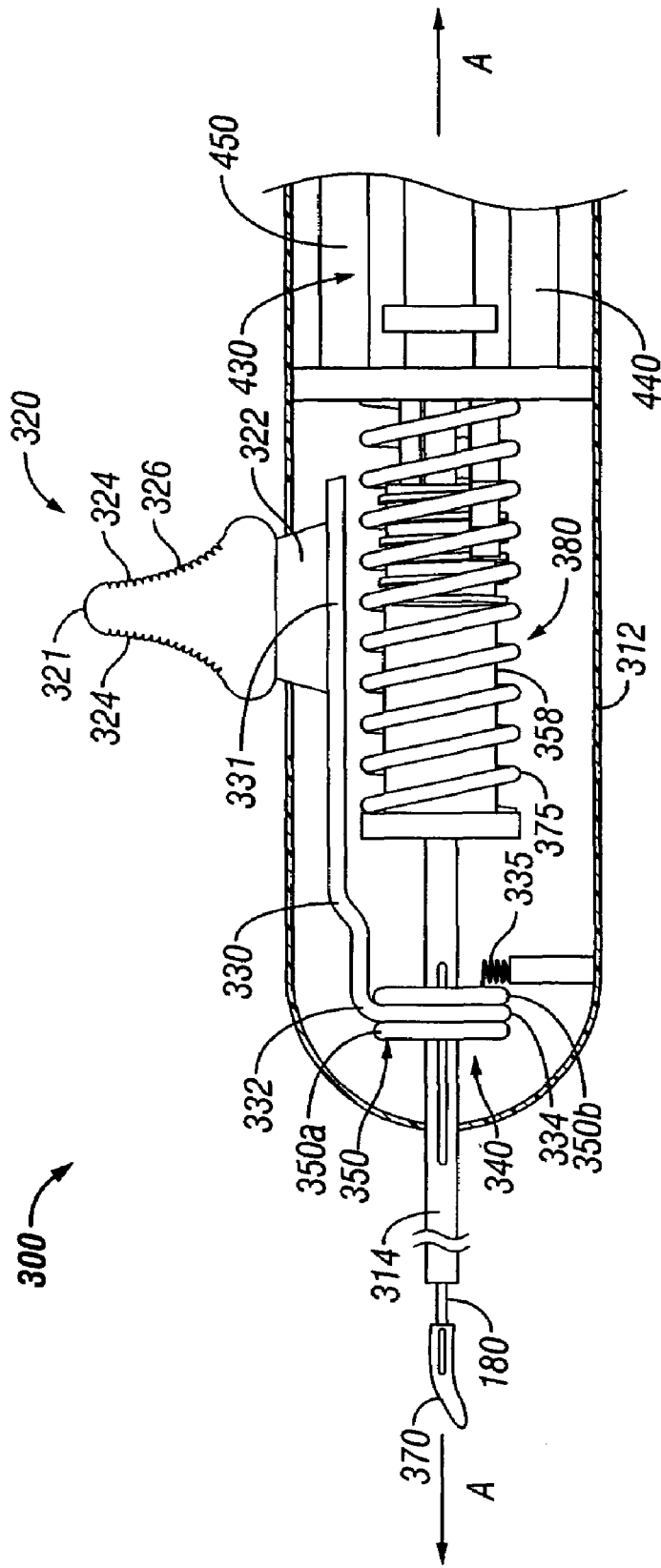
FIG. 3 is an enlarged schematic cross-sectional view of the knife slide of FIG. 1 illustrating an alternate slide trigger.

Referring initially to FIGS. 1-3, illustrations of a slide-activated cutting assembly of a forceps are shown. The slide-activated cutting assembly is generally referred to by reference numeral 320 and the forceps is generally referred to by reference numeral 300. The forceps 300 generally includes a housing 312, a shaft 314 defining axis "A-A," the slide-activated cutting assembly 320, a handle assembly 430 and an end effector assembly 100. The forceps 300 may also include a rotation assembly 80 and a switch 200.

Although the majority of the figure drawings depict the slide-activated cutting assembly 320 for use in connection with endoscopic surgical procedures, the present disclosure may be used for more traditional open surgical procedures. For the purposes herein, the slide-activated cutting assembly 320 is described in terms of an endoscopic instrument, however, it is contemplated that an open version of the slide-activated cutting assembly 320 may also include the same or similar operating components and features as described below.

Referring to FIG. 1, the handle assembly 430 of the forceps 300 includes a fixed handle 450 and a movable handle 440. The fixed handle 450 is integrally associated with the housing 312 and the movable handle 440 is movable relative to the fixed handle 450. The movable handle 440 is operatively connected to the housing 312 and the fixed handle 450. Further details of the handle assembly 430 are discussed in commonly-owned U.S. patent application Ser. No. 10/460,926 and are hereby incorporated by reference herein.

With continued reference to FIG. 1, the rotation assembly 80 may be integrally associated with the housing 312 and may be rotatable approximately 180 degrees in either direction about the axis "A-A." Further details of the rotation assembly 80 are discussed in commonly-owned U.S. patent application Ser. No. 10/460,926 and are hereby incorporated by reference herein.

Figure 5:
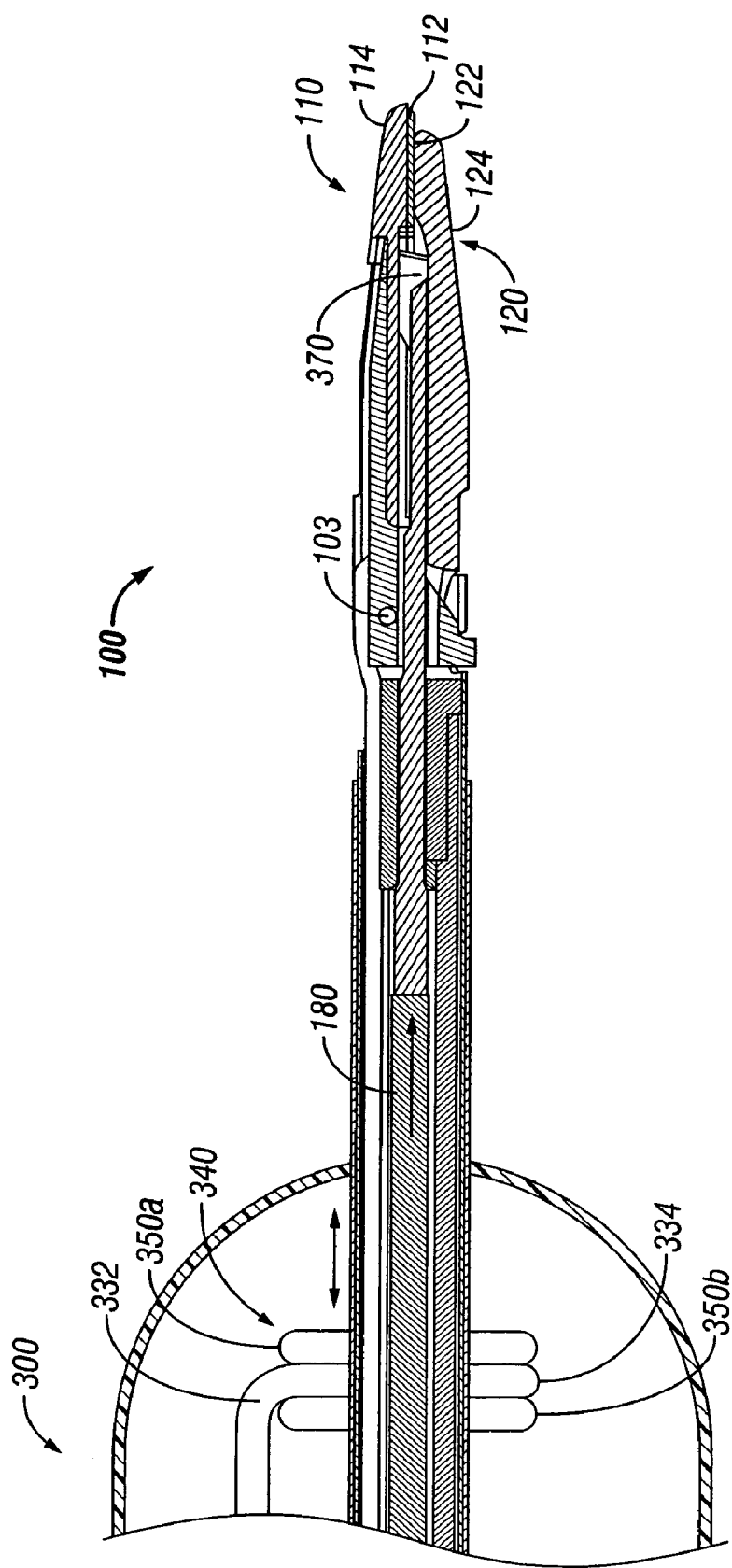
FIG. 5 is an enlarged cross-sectional view of an end effector assembly for use with the slide-activated cutting assembly.
Figure 7:
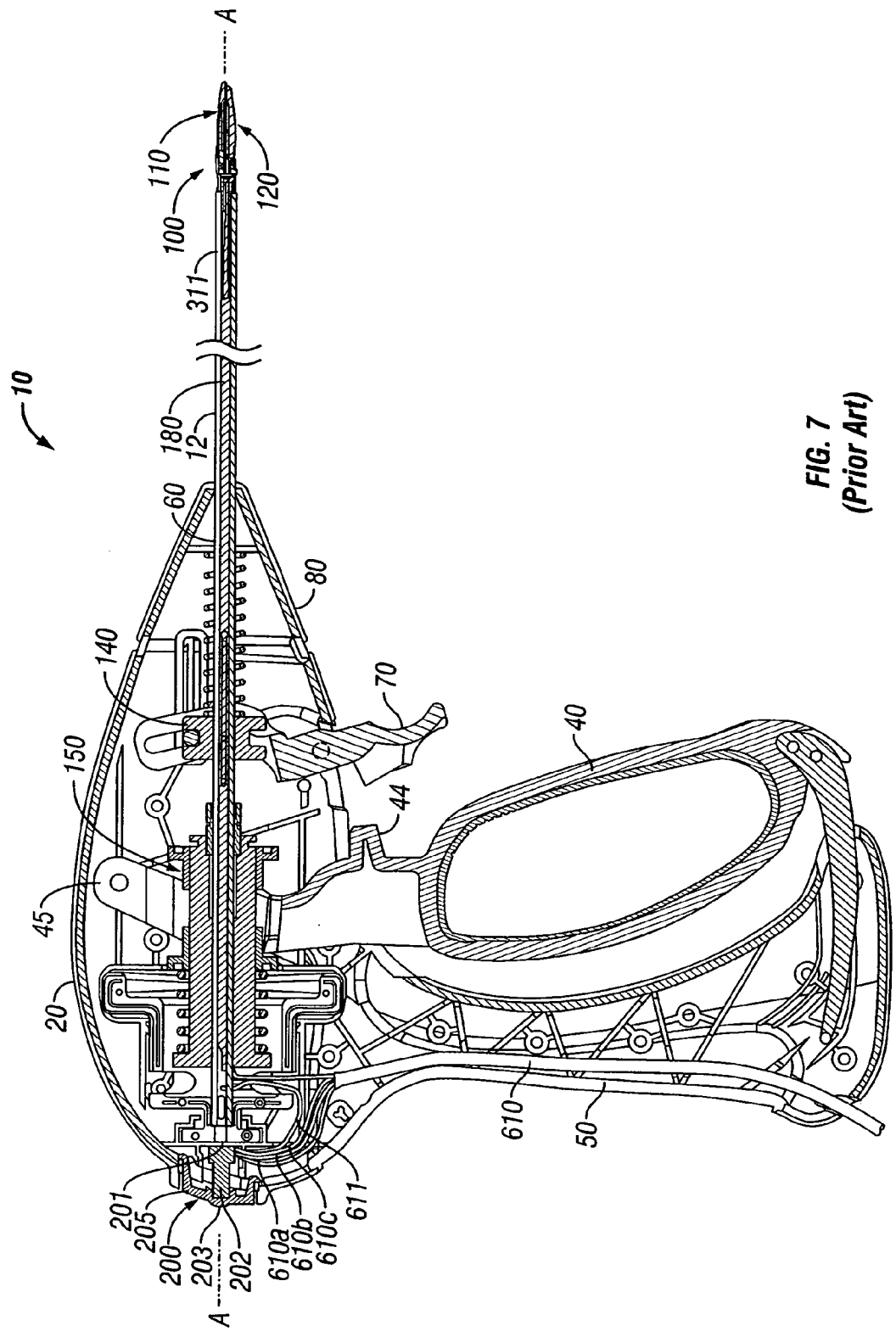
FIG. 7 is a cross-sectional view of the forceps of FIG. 6 as disclosed in prior art.

As best seen in FIGS. 1 and 5, a proximal end 14 of the shaft 314 is in mechanical cooperation with the housing 312. The end effector assembly 100 is attached at a distal end 16 of the shaft 314 and includes a pair of opposing jaw members 110 and 120. The movable handle 440 of the handle assembly 430 is ultimately connected to a drive assembly (illustrated as reference numeral 150 in FIG. 7 depicting Prior Art) which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. Further details of the drive assembly 150 and the end effector assembly 100 are discussed in commonly-owned U.S. patent application Ser. No. 10/460,926 and are hereby incorporated by reference herein.

It is envisioned that the switch 200 permits the user to selectively activate electrosurgical energy in a variety of different orientations, i.e., multi-oriented activation. As can be appreciated, this simplifies activation. Further details of the switch 200 are discussed in commonly-owned U.S. patent application Ser. No. 10/460,926 and are hereby incorporated by reference herein.

When the jaw members 110 and 120 are fully compressed about tissue, the forceps 300 is ready for selective application of electrosurgical energy and subsequent separation of the tissue. More particularly, as energy is being selectively transferred to the end effector assembly 100, across the jaw members 110 and 120 and through the tissue, a tissue seal forms isolating two tissue halves. At this point with other known vessel sealing instruments, the user removes and replaces the forceps 300 with a cutting instrument (not shown) to divide the tissue halves along the tissue seal. As can be appreciated, this is both time consuming and tedious.

As best seen in FIGS. 2 and 3, the slide-activated cutting assembly 320 is in operative engagement with the housing 312 and generally includes a slide trigger 321 and a knife assembly 340 which mutually cooperate to cut tissue. The slide trigger 321 of the slide-activated cutting assembly 320 includes a downwardly depending flange 322 dimensioned to mechanically cooperate with a proximal portion 331 of the knife slide 330 of the knife assembly 340. The slide trigger 321i may include a generally arcuate-shaped finger rest 324 which is designed to facilitate translation thereof by a user.

The knife assembly 340 comprises a knife slide 330, a cutter collar 334 and a collar clamp 350. A distal portion 332 of the knife slide 330 is operatively connected to the cutter collar 334 of the knife assembly 340. The collar clamp 350 is abuttingly positioned against or adjacent the cutter collar 334 and is designed to maintain alignment of the knife assembly 340 during translation of a knife rod 180.

With continued reference to FIGS. 2 and 3, the knife rod 180 is disposed within the shaft 314 which extends distally from the cutter collar 334 to support a knife blade 370 (or other cutting mechanism) and extends proximally through the collar clamp 350 to engage the knife slide 330. The shaft 314 is illustrated secured to a flange 352 which allows distal translation of the knife rod 180 within the shaft 314. It is envisioned that the support flange 352 also holds the shaft 314 in alignment along the axis "A-A." The knife blade 370 is disposed at a distal end of the knife rod 180 for cutting tissue and will be explained in more detail below. A spring 335 may be employed to bias the knife assembly 340, in a proximal-most position relative to the housing 312 and the flange 352.

With continued reference to FIGS. 2 and 3, the knife assembly 340 includes a collar clamp 350 comprising clamps 350a and 350b which secure the distal portion 332 of the knife slide 330, such that distal actuation of the trigger assembly 320 forces the elongated rod 180 distally which, in turn, moves the knife blade 370 distally through tissue, for instance. To cut tissue, the user moves the slide trigger 321 distally to advance the knife slide 330. The clamps 350a and 350b prevent the cutter collar 334 from moving in an angular orientation with respect to axis "A-A," thus preventing a binding effect of the cutter collar 334 on the knife rod 180. In an exemplary embodiment, movement of the cutter collar 334 evenly translates the knife rod 180 and the knife blade 370 along axis "A-A." Further, movement of the slide trigger 321 substantially correlates to the resulting motion of the knife blade 370, i.e., moving the slide trigger 321 one inch distally would move the knife blade 370 one inch in the same direction. It is envisioned that various other ratios may be employed to accomplish the same effect. For example, moving the slide trigger 321 one inch distally may move the knife blade 370 one-half of one inch distally.

As best seen in FIGS. 2 and 3, once assembled, a spring 375 is poised for compression atop a drive housing 358 upon actuation of the handle assembly 430, including handles 440 and 450. More particularly, movement of the handles 440 and 450 reciprocates the drive housing 358 and forces the flange 352 to reciprocate an internally disposed drive rod (not shown) which, in turn, moves jaw members 110 and 120 (see FIG. 5) of the end effector assembly 100 relative to one another. Commonly-owned U.S. patent application Ser. Nos. 10/460,926 and 10/116,944 disclose various conceivable drive mechanisms for reciprocating the drive rod and are both hereby incorporated by reference herein in their entirety.

Figure 6:
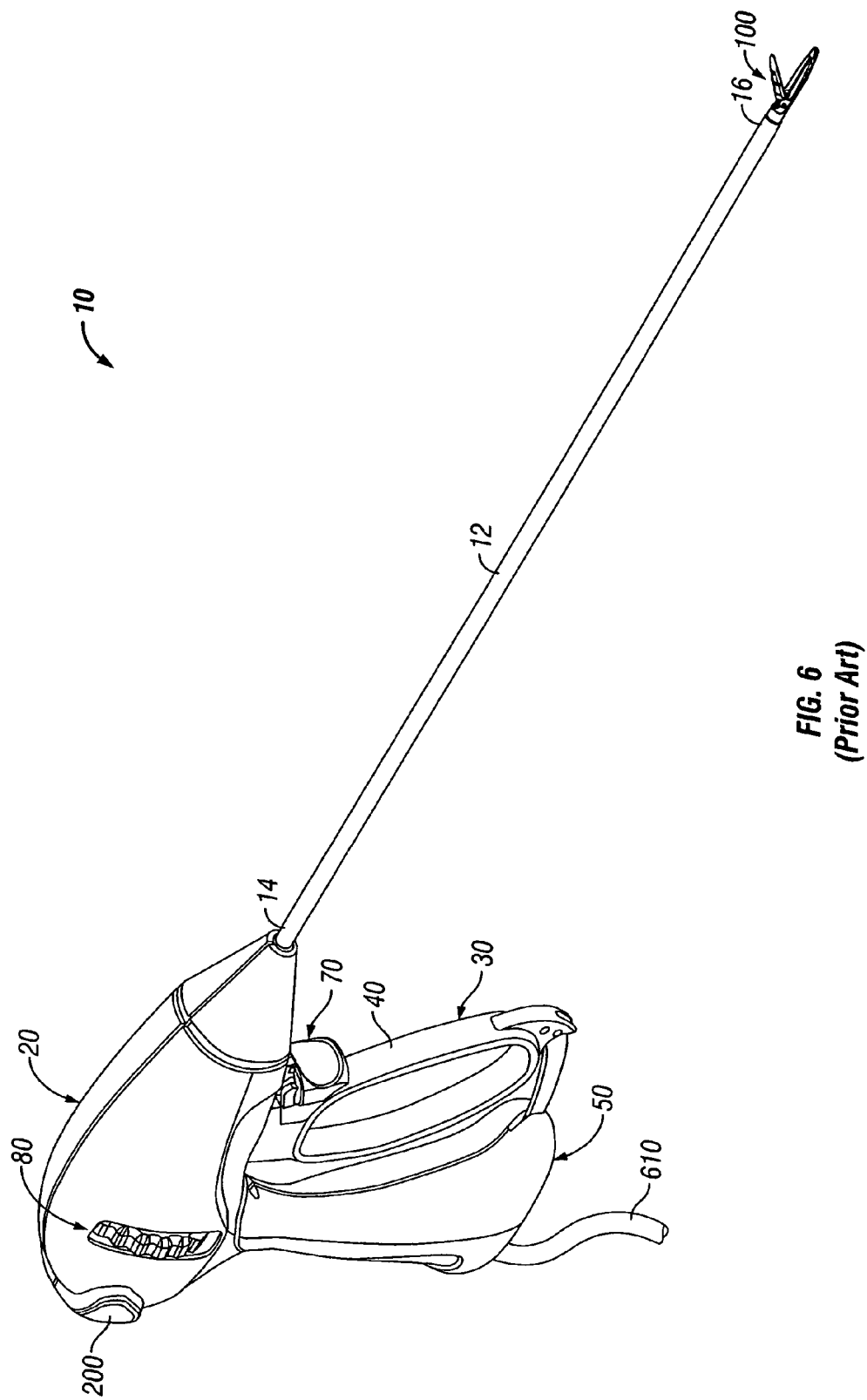
FIG. 6 is a perspective view of an endoscopic bipolar forceps as disclosed in prior art.

The slide-activated cutting assembly 320 of the present disclosure is an in-line, linearly reciprocating type of knife assembly 340. By way of comparison, commonly-owned U.S. patent application Ser. No. 10/460,926 entitled "VESSEL SEALER AND DIVIDER FOR USE WITH SMALL TROCARS AND CANNULAS," shows and describes a trigger assembly with a rotating knife activation, as shown in FIGS. 6 and 7 and further described below.

Figure 4A:
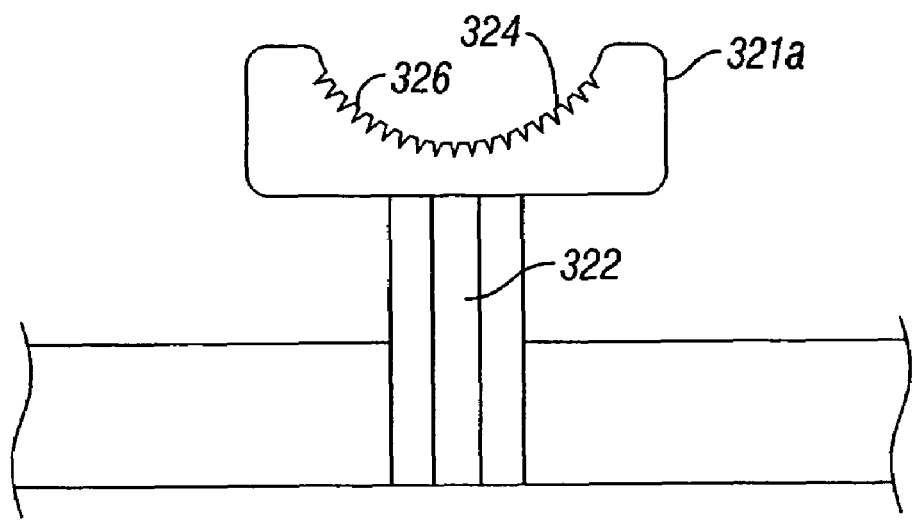
FIG. 4A is an enlarged side view of a slide trigger of FIGS. 1 and 2.
Figure 4B:
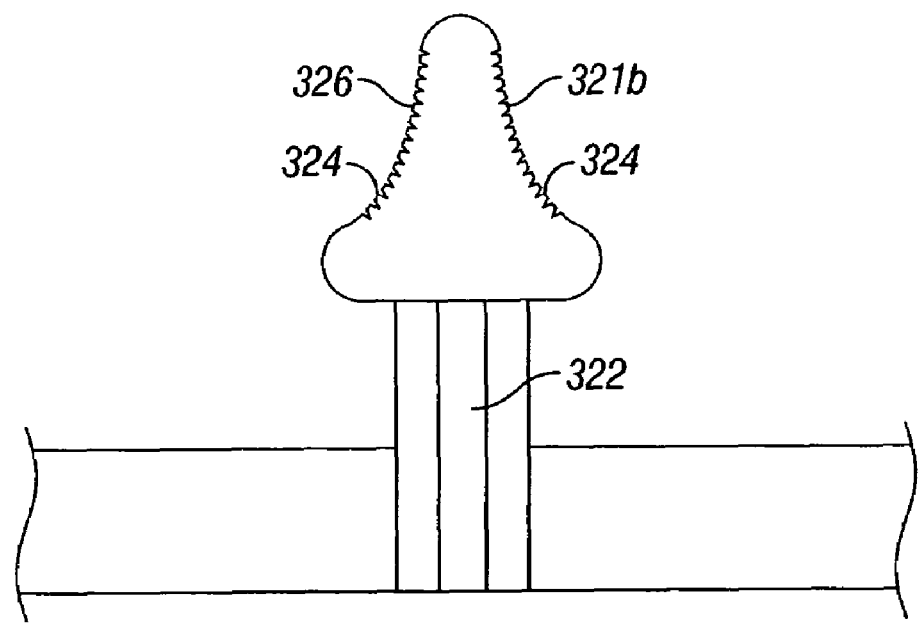
FIG. 4B is an enlarged side view of the alternate embodiment of the slide trigger of FIG. 3.

The present disclosure also allows the operator to pull the slide trigger 321 proximally, which similarly moves the knife blade 370 in a proximal direction. FIGS. 4A and 4B show two envisioned versions of the slide triggers 321a, 321b, respectively. The slide trigger 321a, depicted in FIG. 4A, is dimensioned and configured to allow pushing and pulling (i.e., moving distally and proximally) of the knife rod 180 and the knife blade 370 without the need for the user to change the position of his finger(s) when switching directions. FIG. 4B shows an alternate embodiment of the slide trigger 321b, which is similarly dimensioned and configured to allow pushing and pulling of the knife rod 180 and the knife blade 370. The slide triggers 321a and/or 321b may contain an ergonomically-enhanced gripping element 326 which facilitates gripping of the slide trigger 321a and 321b during activation.

Upon actuation of the slide-activated cutting assembly 320, the knife assembly 340 progressively and selectively divides the tissue along an ideal tissue plane in a precise manner to effectively and reliably divide the tissue into two sealed halves with a tissue gap therebetween. The knife assembly 340 allows the user to quickly separate the tissue after sealing without substituting a cutting instrument through a cannula or trocar port.

It is envisioned that the knife blade 370 may be coupled to the same or an alternative electrosurgical energy source to facilitate separation of the tissue along the tissue seal. Moreover, it is envisioned that the angle of the knife blade 370 may be dimensioned to provide more or less aggressive cutting angles depending upon a particular purpose. For example, the knife blade 370 may be positioned at an angle which reduces "tissue wisps" associated with cutting. Moreover, the knife blade 370 may be designed having different blade geometries such as serrated, notched, perforated, hollow, concave, convex etc., depending upon a particular purpose or to achieve a particular result.

Once the tissue is divided into tissue halves, the jaw members 110 and 120 may be opened by re-grasping the handles 440 and 450. Re-initiation or re-grasping of the handles 440 and 450 reduces the grasping/gripping pressure which, in turn, returns the jaw members 110 and 120 to the open, pre-activated position.

FIGS. 6 and 7 illustrate a prior art embodiment of an endoscopic bipolar forceps shown and described in U.S. patent application Ser. No. 10/460,926, the entire contents of which are hereby incorporated by reference herein. The forceps 10 is shown for use with various surgical procedures and generally includes a housing 20, a handle assembly 30, a rotation assembly 80, a rotating trigger assembly 70 and an end effector assembly 100 which mutually cooperate to grasp, seal and divide tubular vessels and vascular tissue. The forceps 10 also includes a shaft 12 which has a distal end 16 dimensioned to mechanically engage the end effector assembly 100 and a proximal end 14 which mechanically engages the housing 20. The proximal end 14 of shaft 12 is received within the housing 20.

As shown in FIG. 1, the forceps 300 may also include an electrosurgical cable 610 which connects the forceps 300 to a source of electrosurgical energy, e.g., a generator (not shown). Generators such as those sold by Valleylab—a division of Tyco Healthcare LP, located in Boulder Colorado may be used as a source of electrosurgical energy, e.g., FORCE EZ™ Electrosurgical Generator, FORCE FX™ Electrosurgical Generator, FORCE 1C™, FORCE2™ Generator, SurgiStat™ II. One such system is described in commonly-owned U.S. Pat. No. 6,033,399 entitled "ELECTROSURGICAL GENERATOR WITH ADAPTIVE POWER CONTROL," the entire contents of which are hereby incorporated by reference herein. Other systems have been described in commonly-owned U.S. Pat. No. 6,187,003 entitled "BIPOLAR ELECTROSURGICAL INSTRUMENT FOR SEALING VESSELS," the entire contents of which are also incorporated by reference herein. Further details of the electrosurgical cable 610 are illustrated in Prior Art FIG. 7 and are discussed in commonly-owned U.S. patent application Ser. No. 10/460,926 and are hereby incorporated by reference herein.

The generator may include various safety and performance features including isolated output and independent activation of accessories. The electrosurgical generator may include Valleylab's Instant Response™ technology features which provide an advanced feedback system to sense changes in tissue 200 times per second and adjust voltage and current to maintain appropriate power. The Instant Response™ technology is believed to provide one or more of the following benefits to surgical procedure:

Consistent clinical effect through all tissue types;
Reduced thermal spread and risk of collateral tissue damage;
Less need to "turn up the generator"; and
Designed for the minimally invasive environment.

Internal components of the forceps 300 are similar to the internal components illustrated in Prior Art FIG. 7 and described in commonly-owned U.S. patent application Ser. No. 10/460,926 and are hereby incorporated by reference herein. For example, FIG. 6 illustrates the cable 610 internally divided into cable leads 610a, 610b and 610c which each transmit electrosurgical energy through their respective feed paths through the forceps 10 to the end effector assembly 100. Additionally, the handle 40 may include a pair of upper flanges 45 which cooperate with the handle 40 to actuate the drive assembly 150. More particularly, the upper flange 45 may also include a force-actuating flange or drive flange, which abuts the drive assembly 150 such that pivotal movement of the handle 40 forces the actuating flange against the drive assembly 150 which, in turn, closes the jaw members 110 and 120.

As best shown in FIGS. 5 and 7, the end effector assembly 100 which is envisioned to be commonly associated with both the prior art forceps 10 as well as the presently envisioned forceps 300, includes opposing jaw members 110 and 120 which cooperate to effectively grasp tissue (not shown) for sealing purposes. The end effector assembly 100 may be designed as a unilateral assembly, i.e., jaw member 120 is fixed relative to the shaft 12 and jaw member 110 pivots about a pivot pin 103 to grasp tissue or a bilateral assembly where both jaw members 110, 120 move relative to one another. Jaw member 110 includes an outer insulative housing 114 which secures a tissue contacting surface 112. Likewise, jaw member 120 includes an outer insulative housing 124 which secures a tissue contacting surface 122 in opposing relation to surface 112. As such, surfaces 112 and 122 grasp tissue therebetween when the jaw members 110 and 120 are actuated.

It is envisioned that the housing 312, the rotation assembly 80, slide-activated cutting assembly 320, the movable handle 440, the fixed handle 450, and their respective inter-cooperating component parts along with the shaft 314 and the end effector assembly 100 are all assembled during the manufacturing process to form a partially and/or fully disposable forceps 300. For example, the shaft 314 and/or the end effector assembly 100 may be disposable and, therefore, selectively/releasably engagable with the housing 312 and the rotation assembly 80 to form a partially disposable forceps 300 and/or the entire forceps 300 may be disposable after use.

Figure 8:
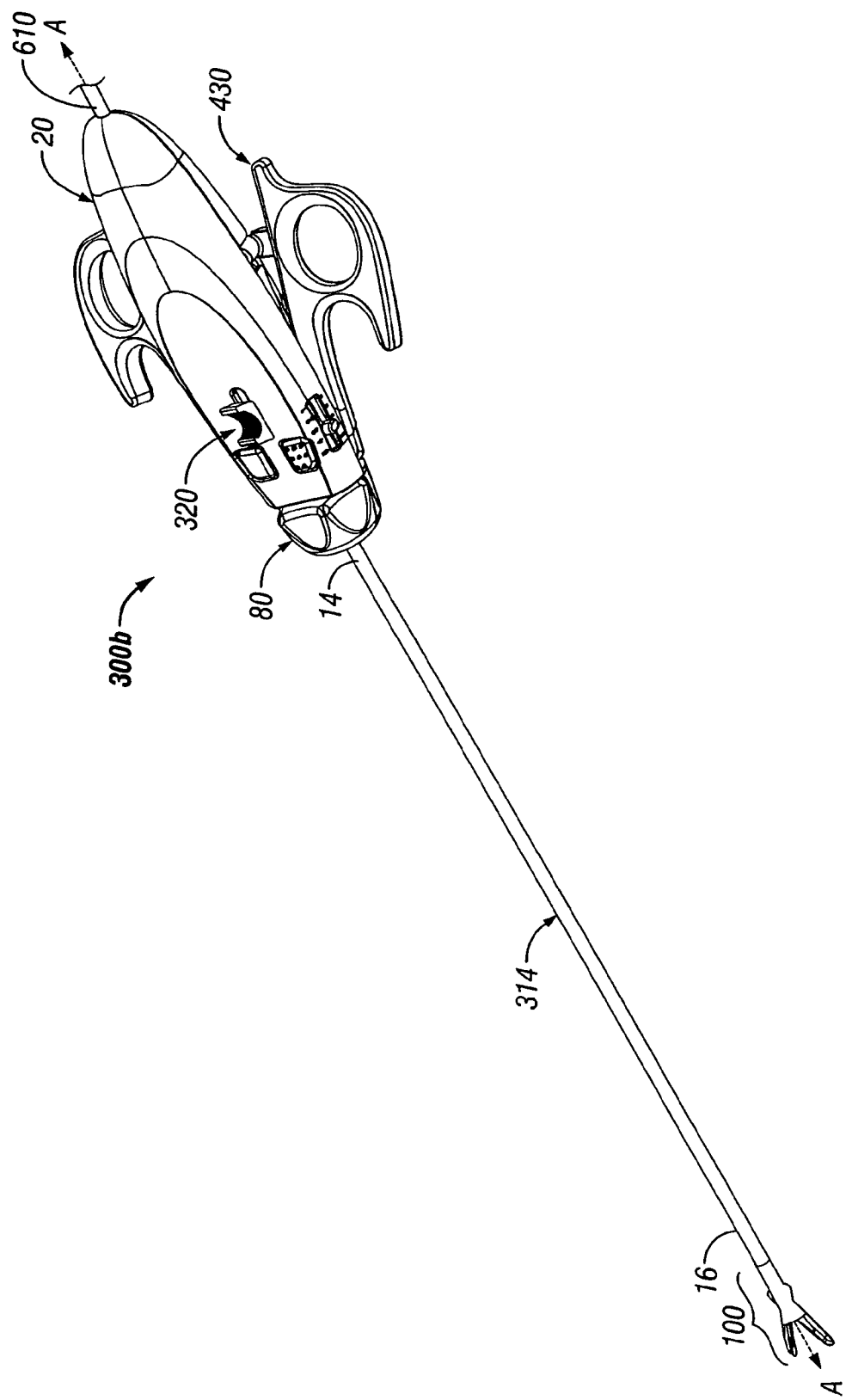
FIG. 8 is a perspective view of an in-line surgical forceps according to an embodiment of the present disclosure.

As illustrated in FIG. 8, the slide-activated cutting assembly 320 may be disposed on an in-line surgical forceps 300b.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of various embodiments. Those skilled in the art will envision other modifications within the scope of the disclosure.

What is claimed is:

1. An endoscopic bipolar forceps, comprising:
   a housing;
   a shaft affixed to the housing comprising an end effector assembly comprising two jaw members at a distal end thereof, the shaft defining a longitudinal axis;
   a drive assembly configured to move at least a portion of the end effector assembly;
   a handle assembly comprising a movable handle adapted to force a drive flange of the movable handle into mechanical cooperation with the drive assembly to move at least a portion of the end effector assembly; and
   a slide-activated cutting assembly disposed at least partially within the housing adapted to move a knife rod comprising a knife blade at a distal end thereof to cut tissue along a tissue seal, the slide-activated cutting assembly further including:
      a slide trigger configured to be pushed distally to move the knife rod distally;
      a knife slide adapted to facilitate translation of the knife rod, a proximal portion of the knife slide being in mechanical engagement with the slide trigger and a distal portion of the knife slide being in mechanical engagement with the knife rod;
      a collar clamp operatively connected to the knife slide adapted to maintain alignment of the knife slide during translation of the knife rod; and
   wherein a source of electrosurgical energy is adapted to connect to each jaw member such that the jaw members are capable of conducting energy through tissue held therebetween to effect a tissue seal.

2. The endoscopic bipolar forceps according to claim 1, wherein the slide trigger is configured to be pulled proximally to move the knife rod proximally.

3. The endoscopic bipolar forceps according to claim 1, wherein the slide trigger comprises a generally arcuate-shaped finger rest.

4. The endoscopic bipolar forceps according to claim 1, wherein the slide-activated cutting assembly further comprises a spring in mechanical engagement with the knife slide which biases the knife slide in a proximal position.

5. The endoscopic bipolar forceps according to claim 1, further comprising a rotating assembly adapted to rotate the jaw members about the longitudinal axis defined by the shaft.

6. The endoscopic bipolar forceps according to claim 1, further comprising a switch disposed within the housing and in electromechanical cooperation with a source of electrosurgical energy, the switch allowing a user to selectively supply bipolar energy to the jaw members to effect the tissue seal.

7. The endoscopic bipolar forceps according to claim 1, wherein the drive assembly comprises a reciprocating sleeve that is adapted to, upon activation of the movable handle, translate one of the jaw members relative to the other jaw member.

8. The endoscopic bipolar forceps according to claim 1, wherein the slide assembly comprises at least one spring adapted to bias the knife rod proximally.

9. The endoscopic bipolar forceps according to claim 1, wherein the forceps is further defined by being in-line.

10. A slide-activated cutting assembly for use with a surgical instrument, comprising:
    a slide trigger comprising a flange; and
    a knife assembly comprising a knife slide, a cutter collar, a knife rod and a collar clamp, the knife slide comprising a proximal portion in mechanical cooperation with the flange of the slide trigger and a distal portion, the cutter collar being operatively connected with the distal portion of the knife slide, the knife rod extending distally from the cutter collar, the collar clamp which maintains alignment of the knife assembly during translation of the knife rod and being positioned adjacent the cutter collar,
    wherein the slide trigger and the knife assembly mutually cooperate to translate the knife rod upon translation of the slide trigger.

11. The slide-activated cutting assembly according to claim 10, wherein the slide trigger comprises a generally arcuate finger rest.

12. The slide-activated cutting assembly according to claim 10, further comprising a knife blade supported on the knife rod.

13. The slide-activated cutting assembly according to claim 10, further comprising a spring adapted to bias the knife assembly proximally.

* * * * *